US006826000B2

(12) United States Patent
Lee et al.

(10) Patent No.: US 6,826,000 B2
(45) Date of Patent: Nov. 30, 2004

(54) OPTICAL FINGERPRINT ACQUISITION APPARATUS

(75) Inventors: Jong Ik Lee, Seoul (KR); Sung Hyu Shin, Seoul (KR); Dong Won Lee, Saratoga, CA (US)

(73) Assignee: SecuGen Corporation, Santa Clara, CA (US)

( * ) Notice: Subject to any disclaimer, the term of this patent is extended or adjusted under 35 U.S.C. 154(b) by 180 days.

(21) Appl. No.: 10/150,419

(22) Filed: May 17, 2002

(65) Prior Publication Data

US 2003/0053228 A1 Mar. 20, 2003

(51) Int. Cl.[7] .............................. G02B 5/04; G06K 9/74
(52) U.S. Cl. ....................... 359/833; 359/837; 359/857; 382/127; 356/71
(58) Field of Search ................................. 359/833, 837, 359/857, 862, 831; 382/127; 356/71

(56) References Cited

U.S. PATENT DOCUMENTS

| 3,383,657 A | 5/1968 | Claassen et al. |
| 3,527,535 A | 9/1970 | Monroe |
| 3,771,124 A | 11/1973 | McMahon |

(List continued on next page.)

FOREIGN PATENT DOCUMENTS

| CA | 1286032 | 9/1991 |
| DE | 195 09 751 | 9/1996 |
| EP | 0 045 915 | 2/1982 |

(List continued on next page.)

OTHER PUBLICATIONS

Seigo Igaki et al. (Jan., 1990). "Holographic Fingerprint Sensor," *FUJITSU–Sci. Tech. J.* 25(4):287–296.

Authen Tec, Inc. Personal Security for the Real World. (Date Unknown). "Comparison of Capacitive and Electric–Field Based Human Fingerprint Readers: The Basic Transducer– Physics," located at: <http://www.authentec.com/efield.html.>.

Isobe, Y. et al. (2001). "Development of Personal Authentication System Using Fingerprint with Digital Signature Technologies," *Proceedings of the 34th Hawaii International Conference on System Sciences*, IEEE pp. 1–9.

Kim, J.H. et al. (2000). "Fingerprint Scanner Using a–Si: H TFT–Array," *SID Digest* pp. 353–355.

(List continued on next page.)

*Primary Examiner*—Ricky D. Shafer
(74) *Attorney, Agent, or Firm*—Morrison & Foerster LLP

(57) ABSTRACT

Disclosed is an optical fingerprint acquisition apparatus capable of reducing an image distortion and a size of an optical system by deforming the shape of a prism. The prism according to the invention includes a fingerprint contacting surface to be touched by a fingerprint of a person, a totally reflecting surface facing the fingerprint contacting surface with an angle $\theta$ for totally and inwardly reflecting the light scattered from the fingerprint in contact with the fingerprint contacting surface, a primarily projecting/re-incident surface linking the fingerprint contacting surface to the totally reflecting surface with an angle $\phi$ for primarily projecting the light totally reflected from the totally reflecting surface so as to be re-incident from outside, and an ultimately projecting surface facing the primarily projecting/re-incident surface for ultimately projecting the light re-incident to the primarily projecting/re-incident surface toward outside.

6 Claims, 1 Drawing Sheet

U.S. PATENT DOCUMENTS

| | | |
|---|---|---|
| 3,864,042 A | 2/1975 | Leventhal |
| 3,865,488 A | 2/1975 | Del Rio |
| 3,873,970 A | 3/1975 | McMahon et al. |
| 3,882,462 A | 5/1975 | McMahon |
| 3,891,968 A | 6/1975 | McMahon |
| 3,947,128 A | 3/1976 | Weinberger et al. |
| 3,968,476 A | 7/1976 | McMahon |
| 3,975,711 A | 8/1976 | McMahon |
| 3,982,836 A | 9/1976 | Green et al. |
| 4,003,656 A | 1/1977 | Leventhal |
| 4,025,898 A | 5/1977 | Shaw |
| 4,120,585 A | 10/1978 | DePalma et al. |
| 4,135,147 A | 1/1979 | Riganati et al. |
| 4,138,058 A | 2/1979 | Atalla |
| 4,140,272 A | 2/1979 | Atalla |
| 4,210,899 A | 7/1980 | Swonger et al. |
| 4,246,568 A | 1/1981 | Peterson |
| 4,253,086 A | 2/1981 | Szwarcbier |
| 4,258,994 A | 3/1981 | Task |
| 4,322,163 A | 3/1982 | Schiller |
| 4,336,998 A | 6/1982 | Ruell |
| 4,338,025 A | 7/1982 | Engel |
| 4,340,300 A | 7/1982 | Ruell |
| 4,353,056 A | 10/1982 | Tsikos |
| 4,358,677 A | 11/1982 | Ruell et al. |
| 4,385,831 A | 5/1983 | Ruell |
| 4,394,773 A | 7/1983 | Ruell |
| 4,414,684 A | 11/1983 | Blonder |
| 4,428,670 A | 1/1984 | Ruell et al. |
| 4,429,413 A | 1/1984 | Edwards |
| 4,455,083 A | 6/1984 | Elmes |
| 4,467,545 A | 8/1984 | Shaw, Jr. |
| 4,486,180 A | 12/1984 | Riley |
| 4,537,484 A | 8/1985 | Fowler et al. |
| 4,544,267 A | 10/1985 | Schiller |
| 4,553,837 A | 11/1985 | Marcus |
| 4,569,080 A | 2/1986 | Schiller |
| 4,577,345 A | 3/1986 | Abramov |
| 4,582,985 A | 4/1986 | Löfberg |
| 4,636,622 A | 1/1987 | Clark |
| 4,668,995 A | 5/1987 | Chen et al. |
| 4,681,435 A | 7/1987 | Kubota et al. |
| 4,681,438 A | 7/1987 | Kaneko |
| 4,684,802 A | 8/1987 | Hakenewerth et al. |
| 4,688,995 A | 8/1987 | Wright et al. |
| 4,701,959 A | 10/1987 | Asai et al. |
| 4,728,186 A * | 3/1988 | Eguchi et al. |
| 4,729,128 A | 3/1988 | Grimes et al. |
| 4,745,268 A | 5/1988 | Drexler |
| 4,768,021 A | 8/1988 | Ferraro |
| 4,783,167 A | 11/1988 | Schiller et al. |
| 4,783,823 A | 11/1988 | Tasaki et al. |
| 4,784,484 A | 11/1988 | Jensen |
| 4,785,171 A | 11/1988 | Dowling, Jr. et al. |
| 4,787,742 A | 11/1988 | Schiller et al. |
| 4,792,226 A | 12/1988 | Fishbine et al. |
| 4,832,485 A | 5/1989 | Bowles |
| 4,835,376 A | 5/1989 | Drexler |
| 4,872,203 A | 10/1989 | Asai et al. |
| 4,876,725 A | 10/1989 | Tomko |
| 4,889,983 A | 12/1989 | Numano et al. |
| 4,905,293 A | 2/1990 | Asai et al. |
| 4,924,085 A * | 5/1990 | Kato et al. |
| 4,925,300 A | 5/1990 | Rachlin |
| 4,932,776 A | 6/1990 | Dowling, Jr. et al. |
| 4,936,680 A | 6/1990 | Henkes et al. |
| 4,946,276 A | 8/1990 | Chilcott |
| 4,977,601 A | 12/1990 | Bicz |
| 4,979,007 A | 12/1990 | Ogawa et al. |
| 4,983,415 A | 1/1991 | Arndt et al. |
| 4,995,086 A | 2/1991 | Lilley et al. |
| 5,050,220 A | 9/1991 | Marsh et al. |
| 5,051,576 A | 9/1991 | Schiller |
| 5,053,608 A | 10/1991 | Senanayake |
| 5,067,162 A | 11/1991 | Driscoll, Jr. et al. |
| 5,077,803 A | 12/1991 | Kato et al. |
| 5,088,817 A * | 2/1992 | Igaki et al. |
| 5,095,194 A | 3/1992 | Barbanell |
| 5,096,290 A | 3/1992 | Ohta |
| 5,103,486 A | 4/1992 | Grippi |
| 5,109,427 A | 4/1992 | Yang |
| 5,138,468 A | 8/1992 | Barbanell |
| 5,144,680 A | 9/1992 | Kobayashi et al. |
| 5,146,102 A | 9/1992 | Higuchi et al. |
| 5,162,644 A | 11/1992 | Nagata et al. |
| 5,175,593 A | 12/1992 | Kumagai et al. |
| 5,177,353 A | 1/1993 | Schiller |
| 5,177,435 A | 1/1993 | Kiyokawa et al. |
| 5,177,802 A | 1/1993 | Fujimoto et al. |
| 5,187,748 A | 2/1993 | Lee |
| 5,189,482 A | 2/1993 | Yang |
| 5,193,855 A | 3/1993 | Shamos |
| 5,210,588 A | 5/1993 | Lee |
| 5,214,699 A | 5/1993 | Monroe et al. |
| 5,222,152 A | 6/1993 | Fishbine et al. |
| 5,222,153 A | 6/1993 | Beiswenger |
| 5,224,173 A | 6/1993 | Kuhns et al. |
| 5,224,174 A | 6/1993 | Schneider et al. |
| 5,229,764 A | 7/1993 | Matchett et al. |
| 5,230,025 A | 7/1993 | Fishbine et al. |
| 5,233,404 A | 8/1993 | Lougheed et al. |
| 5,239,590 A | 8/1993 | Yamamoto |
| 5,241,606 A | 8/1993 | Horie |
| 5,259,025 A | 11/1993 | Monroe et al. |
| 5,261,008 A | 11/1993 | Yamamoto |
| 5,268,963 A | 12/1993 | Monroe et al. |
| 5,280,527 A | 1/1994 | Gullman et al. |
| 5,309,288 A | 5/1994 | Kahre |
| 5,325,442 A | 6/1994 | Knapp |
| 5,343,529 A | 8/1994 | Goldfine et al. |
| 5,349,174 A | 9/1994 | Van Berkel et al. |
| 5,363,453 A | 11/1994 | Gagne et al. |
| 5,373,181 A | 12/1994 | Scheiter et al. |
| 5,386,104 A | 1/1995 | Sime |
| 5,400,662 A | 3/1995 | Tamori |
| 5,416,573 A | 5/1995 | Sartor, Jr. |
| 5,420,936 A | 5/1995 | Fitzpatrick et al. |
| 5,420,937 A | 5/1995 | Davis |
| 5,426,708 A | 6/1995 | Hamada et al. |
| 5,446,290 A | 8/1995 | Fujieda et al. |
| 5,448,649 A | 9/1995 | Chen et al. |
| 5,448,659 A | 9/1995 | Tsutsui et al. |
| 5,456,256 A | 10/1995 | Schneider et al. |
| 5,465,303 A | 11/1995 | Levison et al. |
| 5,467,403 A | 11/1995 | Fishbine et al. |
| 5,480,810 A | 1/1996 | Wei et al. |
| 5,485,312 A | 1/1996 | Horner et al. |
| 5,493,621 A | 2/1996 | Matsumura |
| 5,503,029 A | 4/1996 | Tamori |
| 5,509,083 A | 4/1996 | Abtahi et al. |
| 5,513,272 A | 4/1996 | Bogosian, Jr. |
| 5,515,298 A | 5/1996 | Bicz |
| 5,515,738 A | 5/1996 | Tamori |
| 5,524,161 A | 6/1996 | Omori et al. |
| 5,526,701 A | 6/1996 | Tamori |
| 5,541,994 A | 7/1996 | Tomko et al. |
| 5,546,471 A | 8/1996 | Merjanian |
| 5,548,394 A | 8/1996 | Giles et al. |
| 5,559,504 A | 9/1996 | Itsumi et al. |
| 5,563,345 A | 10/1996 | Kersten et al. |
| 5,587,533 A | 12/1996 | Schneider et al. |

| | | |
|---|---|---|
| 5,596,454 A | 1/1997 | Hebert |
| 5,598,474 A | 1/1997 | Johnson |
| 5,603,179 A | 2/1997 | Adams |
| 5,619,586 A | 4/1997 | Sibbald |
| 5,621,516 A | 4/1997 | Shinzaki et al. |
| 5,623,552 A | 4/1997 | Lane |
| 5,623,553 A | 4/1997 | Sekiya |
| 5,625,448 A | 4/1997 | Ranalli et al. |
| 5,629,764 A | 5/1997 | Bahuguna et al. |
| 5,635,723 A | 6/1997 | Fujieda et al. |
| 5,644,645 A | 7/1997 | Osuga |
| 5,648,648 A | 7/1997 | Chou et al. |
| 5,650,842 A | 7/1997 | Maase et al. |
| 5,680,205 A | 10/1997 | Borza |
| 5,680,460 A | 10/1997 | Tomko et al. |
| 5,686,765 A | 11/1997 | Washington |
| 5,689,576 A | 11/1997 | Schneider et al. |
| 5,701,770 A | 12/1997 | Cook et al. |
| 5,708,497 A | 1/1998 | Fujieda |
| 5,712,912 A | 1/1998 | Tomko et al. |
| 5,721,583 A | 2/1998 | Harada et al. |
| 5,729,334 A | 3/1998 | Van Ruyven |
| 5,732,148 A | 3/1998 | Keagy et al. |
| 5,736,734 A | 4/1998 | Marcus et al. |
| 5,737,071 A | 4/1998 | Arndt |
| 5,737,420 A | 4/1998 | Tomko et al. |
| 5,737,439 A | 4/1998 | Lapsley et al. |
| 5,740,276 A | 4/1998 | Tomko et al. |
| 5,745,046 A | 4/1998 | Itsumi et al. |
| 5,748,765 A | 5/1998 | Takhar |
| 5,748,766 A | 5/1998 | Maase et al. |
| 5,757,278 A | 5/1998 | Itsumi |
| 5,761,330 A | 6/1998 | Stoianov et al. |
| 5,764,347 A | 6/1998 | Podmaniczky et al. |
| 5,778,089 A | 7/1998 | Borza |
| 5,781,651 A | 7/1998 | Hsiao et al. |
| 5,790,668 A | 8/1998 | Tomko |
| 5,796,857 A | 8/1998 | Hara |
| 5,796,858 A | 8/1998 | Zhou et al. |
| 5,808,729 A | 9/1998 | Sugawara et al. |
| 5,812,252 A | 9/1998 | Bowker et al. |
| 5,815,252 A | 9/1998 | Price-Francis |
| 5,815,598 A | 9/1998 | Hara et al. |
| 5,818,956 A | 10/1998 | Tuli |
| 5,822,445 A | 10/1998 | Wong |
| 5,825,005 A | 10/1998 | Behnke |
| 5,825,474 A | 10/1998 | Maase |
| 5,828,773 A | 10/1998 | Setlak et al. |
| 5,832,091 A | 11/1998 | Tomko et al. |
| 5,838,206 A | 11/1998 | Busca et al. |
| 5,838,306 A | 11/1998 | O'Connor et al. |
| 5,841,907 A | 11/1998 | Javidi et al. |
| 5,844,287 A | 12/1998 | Hassan et al. |
| 5,847,876 A | 12/1998 | Ferrante et al. |
| 5,848,231 A | 12/1998 | Teitelbaum et al. |
| 5,852,670 A | 12/1998 | Setlak et al. |
| 5,859,420 A | 1/1999 | Borza |
| 5,862,248 A | 1/1999 | Salatino et al. |
| 5,867,802 A | 2/1999 | Borza |
| 5,869,822 A | 2/1999 | Meadows, II et al. |
| 5,875,025 A | 2/1999 | Toyoda et al. |
| 5,879,454 A | 3/1999 | Peng |
| 5,892,599 A | 4/1999 | Bahuguna |
| 5,900,993 A | 5/1999 | Betensky |
| 5,903,225 A | 5/1999 | Schmitt et al. |
| 5,907,627 A | 5/1999 | Borza |
| 5,920,384 A | 7/1999 | Borza |
| 5,920,640 A | 7/1999 | Salatino et al. |
| 5,920,642 A | 7/1999 | Merjanian |
| 5,926,261 A | 7/1999 | Hoshino |
| 5,937,557 A | 8/1999 | Bowker et al. |
| 5,938,706 A | 8/1999 | Feldman |
| 5,940,525 A | 8/1999 | Itsumi |
| 5,940,526 A | 8/1999 | Setlak et al. |
| 5,942,761 A | 8/1999 | Tuli |
| 5,952,588 A | 9/1999 | Young |
| 5,953,441 A | 9/1999 | Setlak |
| 5,953,442 A | 9/1999 | Dydyk et al. |
| 5,956,415 A | 9/1999 | McCalley et al. |
| 5,963,656 A | 10/1999 | Boll et al. |
| 5,963,657 A | 10/1999 | Bowker et al. |
| 5,963,679 A | 10/1999 | Setlak |
| 5,970,405 A | 10/1999 | Kaplan et al. |
| 5,974,162 A | 10/1999 | Metz et al. |
| 5,978,495 A | 11/1999 | Thomopoulos et al. |
| 5,978,496 A | 11/1999 | Harkin |
| 5,982,894 A | 11/1999 | McCalley et al. |
| 5,986,746 A | 11/1999 | Metz et al. |
| 5,991,145 A | 11/1999 | Lagrotta et al. |
| 5,991,431 A | 11/1999 | Borza et al. |
| 5,991,467 A | 11/1999 | Kamiko |
| 5,995,630 A | 11/1999 | Borza |
| 6,002,499 A | 12/1999 | Corboline et al. |
| 6,002,770 A | 12/1999 | Tomko et al. |
| 6,005,962 A | 12/1999 | Hirota et al. |
| 6,006,328 A | 12/1999 | Drake |
| 6,011,860 A | 1/2000 | Fujieda et al. |
| 6,044,128 A | 3/2000 | Tanaka et al. |
| 6,115,483 A | 9/2000 | Suga |
| 6,115,484 A | 9/2000 | Bowker et al. |
| 6,122,394 A | 9/2000 | Neukermans et al. |
| 6,127,674 A * | 10/2000 | Shinzaki et al. |
| 6,150,665 A | 11/2000 | Suga |
| 6,154,285 A | 11/2000 | Teng et al. |
| 6,175,641 B1 | 1/2001 | Kalló et al. |
| 6,185,319 B1 | 2/2001 | Fujiwara |
| 6,239,468 B1 | 5/2001 | Chang et al. |
| 6,300,977 B1 | 10/2001 | Waechter et al. |
| 6,324,020 B1 | 11/2001 | Teng et al. |
| 6,327,376 B1 | 12/2001 | Harkin |
| 6,381,347 B1 | 4/2002 | Teng et al. |
| 6,401,551 B1 | 6/2002 | Kawahara et al. |
| 6,462,563 B1 | 10/2002 | Kawahara et al. |
| 6,463,166 B1 | 10/2002 | Fujiwara |
| 6,501,529 B1 | 12/2002 | Kurihara et al. |
| 6,552,764 B2 | 4/2003 | Fujioka et al. |
| 2002/0000915 A1 | 1/2002 | Lee et al. |
| 2002/0110266 A1 | 8/2002 | Teng et al. |
| 2002/0163601 A1 | 11/2002 | Min et al. |
| 2003/0053228 A1 | 3/2003 | Lee et al. |

FOREIGN PATENT DOCUMENTS

| | | |
|---|---|---|
| EP | 0 308 162 | 3/1989 |
| EP | 0 617 919 | 10/1994 |
| EP | 0 640 933 | 3/1995 |
| EP | 0 847 024 | 6/1998 |
| EP | 0 867 828 | 9/1998 |
| EP | 0 867 829 | 9/1998 |
| JP | 55-013446 | 1/1980 |
| JP | 58-076705 | 5/1983 |
| JP | 58-144280 | 8/1983 |
| JP | 58-201178 | 11/1983 |
| JP | 59-053975 | 3/1984 |
| JP | 59-103175 | 6/1984 |
| JP | 59-139481 | 8/1984 |
| JP | 59-142675 | 8/1984 |
| JP | 59-204109 | 11/1984 |
| JP | 60-050406 | 3/1985 |
| JP | 61-043380 | 3/1986 |
| JP | 61-045371 | 3/1986 |
| JP | 61-059574 | 3/1986 |
| JP | 61-145686 | 7/1986 |

| | | | | | | |
|---|---|---|---|---|---|---|
| JP | 61-151788 | 7/1986 | | JP | 01-180686 | 7/1989 |
| JP | 61-153779 | 7/1986 | | JP | 01-205392 | 8/1989 |
| JP | 61-175866 | 8/1986 | | JP | 01-205393 | 8/1989 |
| JP | 61-175868 | 8/1986 | | JP | 01-223576 | 9/1989 |
| JP | 61-198211 | 9/1986 | | JP | 01-254827 | 10/1989 |
| JP | 61-201380 | 9/1986 | | JP | 01-262838 | 10/1989 |
| JP | 61-221883 | 10/1986 | | JP | 01-287786 | 11/1989 |
| JP | 61-240383 | 10/1986 | | JP | 01-307886 | 12/1989 |
| JP | 61-292786 | 12/1986 | | JP | 01-314383 | 12/1989 |
| JP | 62-020081 | 1/1987 | | JP | 02-001242 | 1/1990 |
| JP | 62-042285 | 2/1987 | | JP | 02-050782 | 2/1990 |
| JP | 62-063381 | 3/1987 | | JP | 02-126381 | 5/1990 |
| JP | 62-072081 | 4/1987 | | JP | 2-133892 | 5/1990 |
| JP | 62-074171 | 4/1987 | | JP | 02-146691 | 6/1990 |
| JP | 62-074172 | 4/1987 | | JP | 02-149253 | 6/1990 |
| JP | 62-074175 | 4/1987 | | JP | 02-161931 | 6/1990 |
| JP | 62-074176 | 4/1987 | | JP | 02-164340 | 6/1990 |
| JP | 62-074177 | 4/1987 | | JP | 02-167138 | 6/1990 |
| JP | 62-079488 | 4/1987 | | JP | 2-176894 | 7/1990 |
| JP | 62-090780 | 4/1987 | | JP | 02176984 * | 7/1990 |
| JP | 62-121587 | 6/1987 | | JP | 2-188888 | 7/1990 |
| JP | 62-121588 | 6/1987 | | JP | 02-194485 | 8/1990 |
| JP | 62-123580 | 6/1987 | | JP | 02-226493 | 9/1990 |
| JP | 62-154075 | 7/1987 | | JP | 02-270087 | 11/1990 |
| JP | 62-191816 | 8/1987 | | JP | 02-270088 | 11/1990 |
| JP | 62-206687 | 9/1987 | | JP | 02-277182 | 11/1990 |
| JP | 62-206688 | 9/1987 | | JP | 03-092983 | 4/1991 |
| JP | 62-206689 | 9/1987 | | JP | 03-092984 | 4/1991 |
| JP | 62-209686 | 9/1987 | | JP | 3-095693 | 4/1991 |
| JP | 62-235691 | 10/1987 | | JP | 03-100785 | 4/1991 |
| JP | 62-266686 | 11/1987 | | JP | 03-110689 | 5/1991 |
| JP | 63-000678 | 1/1988 | | JP | 03-113686 | 5/1991 |
| JP | 63-000679 | 1/1988 | | JP | 03-154182 | 7/1991 |
| JP | 63-065578 | 3/1988 | | JP | 03-176719 | 7/1991 |
| JP | 63-074026 | 4/1988 | | JP | 03-194675 | 8/1991 |
| JP | 63-124176 | 5/1988 | | JP | 03-194676 | 8/1991 |
| JP | 63-124177 | 5/1988 | | JP | 03-194677 | 8/1991 |
| JP | 63-156294 | 6/1988 | | JP | 03-217992 | 9/1991 |
| JP | 63-165982 | 7/1988 | | JP | 03-244092 | 10/1991 |
| JP | 63-177279 | 7/1988 | | JP | 3-246693 | 11/1991 |
| JP | 63-204374 | 8/1988 | | JP | 03-246778 | 11/1991 |
| JP | 63-205777 | 8/1988 | | JP | 3-292578 | 12/1991 |
| JP | 63-220216 | 9/1988 | | JP | 4-24881 | 1/1992 |
| JP | 63-221483 | 9/1988 | | JP | 04024881 * | 1/1992 |
| JP | 63-221484 | 9/1988 | | JP | 04-088586 | 3/1992 |
| JP | 63-221485 | 9/1988 | | JP | 04-092990 | 3/1992 |
| JP | 63-223875 | 9/1988 | | JP | 04-120671 | 4/1992 |
| JP | 63-228270 | 9/1988 | | JP | 04-125780 | 4/1992 |
| JP | 63-228271 | 9/1988 | | JP | 04-182879 | 6/1992 |
| JP | 63-269258 | 11/1988 | | JP | 04-190470 | 7/1992 |
| JP | 63-273975 | 11/1988 | | JP | 04-230583 | 8/1992 |
| JP | 63-273976 | 11/1988 | | JP | 04-242486 | 8/1992 |
| JP | 63-292275 | 11/1988 | | JP | 04-252383 | 9/1992 |
| JP | 63-298484 | 12/1988 | | JP | 04-271477 | 9/1992 |
| JP | 63-301368 | 12/1988 | | JP | 04-271478 | 9/1992 |
| JP | 63-301369 | 12/1988 | | JP | 04-320899 | 11/1992 |
| JP | 63-307586 | 12/1988 | | JP | 04-367984 | 12/1992 |
| JP | 63-310087 | 12/1988 | | JP | 05-101168 | 4/1993 |
| JP | 63-311484 | 12/1988 | | JP | 05-168610 | 7/1993 |
| JP | 01-013677 | 1/1989 | | JP | 05-216891 | 8/1993 |
| JP | 01-013678 | 1/1989 | | JP | 5-216981 | 8/1993 |
| JP | 01-037934 | 2/1989 | | JP | 05-242230 | 9/1993 |
| JP | 01-046172 | 2/1989 | | JP | 05266174 * | 10/1993 |
| JP | 01-058069 | 3/1989 | | JP | 05298431 * | 11/1993 |
| JP | 01-068894 | 3/1989 | | JP | 06-195450 | 7/1994 |
| JP | 01-076376 | 3/1989 | | JP | 06-282636 | 10/1994 |
| JP | 01-094418 | 4/1989 | | JP | 7-131322 | 5/1995 |
| JP | 01-119881 | 5/1989 | | JP | 07-171137 | 7/1995 |
| JP | 01-119882 | 5/1989 | | JP | 07-208001 | 8/1995 |
| JP | 01-134687 | 5/1989 | | JP | 07-220041 | 8/1995 |
| JP | 01-180685 | 7/1989 | | JP | 07-262380 | 10/1995 |

| | | |
|---|---|---|
| JP | 07-308308 | 11/1995 |
| JP | 07-319059 | 12/1995 |
| JP | 07-331939 | 12/1995 |
| JP | 08-138046 | 5/1996 |
| JP | 09-134419 | 5/1997 |
| JP | 10-014904 | 1/1998 |
| JP | 11-102432 | 4/1999 |
| JP | 11-203041 | 7/1999 |
| KR | 1993-242230 | 9/1993 |
| KR | 94-7344 | 8/1994 |
| KR | 1996-011690 | 4/1996 |
| KR | 10-2000-0050137 | 8/2000 |
| KR | 10-2000-0063878 | 11/2000 |
| KR | 10-2001-0000324 | 1/2001 |
| KR | 10-2001-0000508 | 1/2001 |
| KR | 10-2001-0002816 | 1/2001 |
| KR | 10-2001-0035260 | 5/2001 |
| KR | 10-2001-0035295 | 5/2001 |
| KR | 10-2001-0057120 | 7/2001 |
| KR | 10-2001-0074375 | 8/2001 |
| KR | 10-2001-0080832 | 8/2001 |
| KR | 10-2001-0083355 | 9/2001 |
| WO | WO 96/13800 | 5/1996 |
| WO | WO 97/14111 | 4/1997 |
| WO | WO 98/11478 | 3/1998 |
| WO | WO 98/11501 | 3/1998 |
| WO | WO 98/11750 | 3/1998 |
| WO | WO 98/35118 | 8/1998 |
| WO | WO 00/08591 | 2/2000 |
| WO | WO 00/28469 | 5/2000 |
| WO | WO 00/38099 | 6/2000 |
| WO | WO 01/11549 | 2/2001 |
| WO | WO 01/69520 | 9/2001 |
| WO | WO 2004/019382 | 3/2004 |

OTHER PUBLICATIONS

Pettersson, M. et al. (Nov. 16, 2001). "Ensuring Integrity with Fingerprint Verification," *Precise Biometrics AB* pp. 1–5.

Ruiz–Mezcua, B. et al. (1999). "Biometrics Verification in a Real Environment," *IEEE* pp. 243–246.

Sanchez–Reillo, R. et al. (February, 2000). "Acces Control System with Hand Geometry Verification and Smart Cards, "*IEEE AES Systems Magazine* pp. 45–48.

Verlinde, P. et al. (2000). "Multi–Modal Identity Verification Using Expert Fusion," *Information Fusion* 1:17–33.

* cited by examiner

OPTICAL FINGERPRINT ACQUISITION APPARATUS

BACKGROUND OF THE INVENTION

1. Related Applications

The present application claims priority to Korean Application No. 2001-57070, filed Sep. 17, 2001, entitled "Optical Fingerprint Acquisition Apparatus" by Jong Ik Lee, Sung Hyu Shin and Dong Won Lee and incorporate that application by reference.

2. Field of the Invention

The present invention relates to an optical fingerprint acquisition apparatus, and in particular, to an optical fingerprint acquisition apparatus capable of reducing an image distortion and a size of an optical system by deforming the shape of a prism.

3. Description of the Related Art

A fingerprint acquisition apparatus is an apparatus for acquiring fingerprints applicable to a fingerprint recognizer, which is employed in personnel airlocks, safe locking devices, access control, time attendance, computer access control, etc., by comparing an acquired fingerprint with a user's pre-registered fingerprint. The fingerprint acquisition apparatus is roughly classified into an optical type and a non-optical type.

An optical fingerprint acquisition apparatus is an apparatus for irradiating light onto a fingerprint laid on a prism for forming an image, and reading a fingerprint image formed on an image sensor after being reflected in accordance with the shape of the valleys or ridges of the fingerprint so as to be compared with a pre-stored fingerprint. FIG. 1 shows a mechanism of a typical optical fingerprint acquisition apparatus.

The fingerprint acquisition apparatus in FIG. 1 represents a "scattering type" fingerprint acquisition apparatus, which comprises an image forming prism 1, a light source 3, a condensing lens 4, and an image sensor 5. The light is incident from the light source 3 to a fingerprint acquisition window 2 of the image forming prism 1 at a perpendicular angle or an angle much less than a critical angle. Therefore, the light passes through the fingerprint acquisition window 2 without reaching the image sensor at the ridges of the fingerprint that do not reach the fingerprint acquisition window 2, while the incident light is reflected and scattered from the valleys of the fingerprint. The scattered light is incident to the condensing lens 4 and detected by the image sensor 5. Accordingly, the amount of light incident from the valleys of a fingerprint to the image sensor 5 is discriminated from the amount of light incident from the ridges of a fingerprint to the image sensor 5. As a consequence, the image sensor 5 outputs electric signals of different levels in accordance with the pattern of the fingerprint. An image processor (not shown in the drawing) defines and processes an output value of the image sensor 5 by a digital signal so as to recognize patterns of the fingerprint.

Meanwhile, there has been a strong demand for reducing the size of a fingerprint acquisition apparatus in conformity with the recent trend of minimizing sizes of products. In particular, the demand is focused on reducing the size of each component as well as of an optical path. However, since it is impossible to reduce the size of human fingers and fingerprints, there is a limit to reduce the size of each component. Moreover, reducing the length of an optical path to exceed a necessary extent results in serious deterioration of the quality of a fingerprint image.

Japanese Laid-Open Patent Publication No. Hei 4-24881 (Jan. 28, 1992) discloses a method of changing the optical path to diverse directions within an image forming prism. Japanese Laid-Open Patent Publication No. Hei 2-176984 (Jul. 10, 1990) discloses a method for changing an optical path in diverse manners inside of an image forming prism and a method for correcting an image projected from the image forming prism by using a correction lens and a correction prism.

Thus, ongoing researches are being made to seek a method for correcting an image distortion in addition to a method for forming and projecting a fingerprint image. The distance (optical path) between an image sensor and a fingerprint is variable depending on a position of the fingerprint on the prism of an optical fingerprint acquisition apparatus. Therefore, the fingerprint image is distorted from its actual image at a position where an ultimate image is formed and phased open. The distortion often appears in a trapezoidal shape.

To minimize such an image distortion, distortion and astigmatism of an image are corrected by combining a condensing lens for condensing a fingerprint image projected from a prism with a correction lens or a correction prism. In that case, however, the optical system becomes larger. In other words, size of the fingerprint acquisition apparatus cannot be reduced because the condensing lens, image correction prism, path changing mirror, etc. are discretely installed. This ultimately results in an increase of the manufacturing cost and a decrease of the productivity.

A desirable solution to reduce image distortion while maintaining size of the optical system to be small is to unify the distance (length of the optical path) from any position of the fingerprint to the image sensor.

SUMMARY OF THE INVENTION

It is, therefore, an object of the present invention to provide an optical fingerprint acquisition apparatus employing a prism and a reflecting mirror that can unify the distance (length of the optical path) from any position of a fingerprint to an image sensor to minimize the optical path difference without relying on a lens or a prism for image correction.

To achieve the above and other objects of the present invention, there is provided a fingerprint acquisition apparatus for acquiring a fingerprint image by means of light scattered from valleys and ridges of a fingerprint, the apparatus comprising a prism and a reflecting mirror.

The prism comprises: a fingerprint contacting surface to be touched by a fingerprint of a person; a totally reflecting surface facing the fingerprint contacting surface for totally and inwardly reflecting the light scattered from the fingerprint in contact with the fingerprint contacting surface; a primarily projecting/re-incident surface linking the fingerprint contacting surface to the totally reflecting surface for primarily projecting the light totally reflected from the totally reflecting surface so as to be re-incident from outside; and an ultimately projecting surface facing the primarily projecting/re-incident surface for ultimately projecting the light re-incident to the primarily projecting/re-incident surface toward outside.

The reflecting mirror is installed outside adjacent to the primarily projecting/re-incident surface of the prism so as to correct the optical path difference by reflecting the light projected from the primarily projecting/re-incident surface so as to be re-incident to the primarily projecting/re-incident surface.

The prism is preferably shaped rectangular, and each surface thereof preferably has the following relation.

(Length of the Ultimately Projecting Surface)<(Length of the Primarily Projecting/Re-Incident Surface)<(Length of the Fingerprint Contacting Surface)<(Length of the Totally Reflecting Surface)

BRIEF DESCRIPTION OF THE DRAWINGS

The other objects, features and advantages of the present invention will now become more apparent from the following detailed description when taken in conjunction with the accompanying drawings, in which.

DETAILED DESCRIPTION OF THE PREFERRED EMBODIMENT

A preferred embodiment of the present invention will be described herein below with reference to the accompanying drawing. In the following description, well-known functions or constructions are not described in detail since they would obscure the invention in unnecessary detail.

Figure 1:
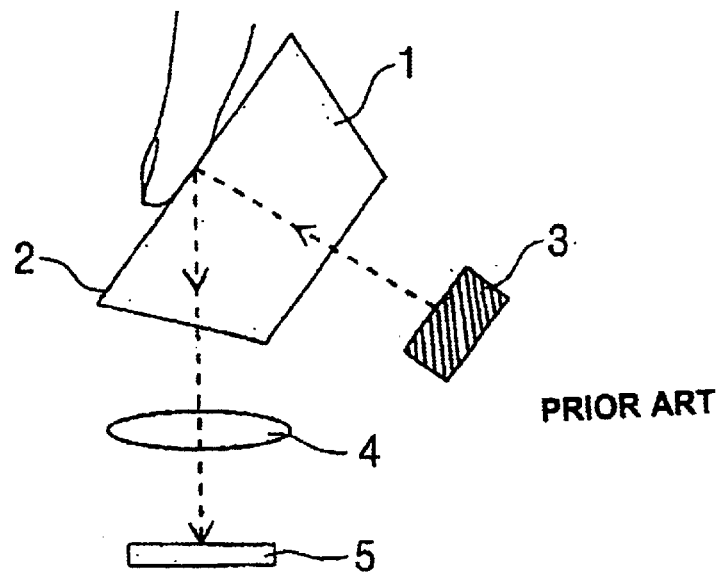
FIG. 1 is a diagram illustrating construction of a conventional fingerprint acquisition apparatus.
Figure 2:
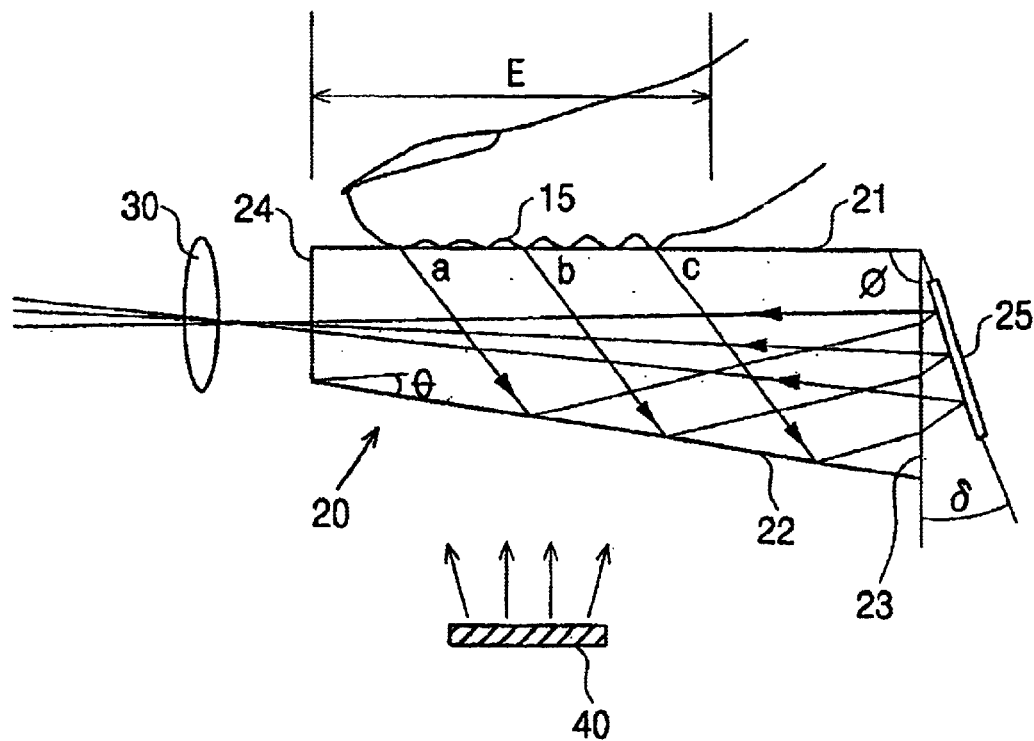
FIG. 2 is a diagram illustrating construction of an optical fingerprint acquisition apparatus according to the present invention.

FIG. 2 shows a fingerprint acquisition apparatus, including a prism 20 for forming a fingerprint image by means of light scattered from valleys and ridges of a fingerprint, a condensing lens 30 and a light source 40, according to an embodiment of the present invention.

The prism 20 employed in the embodiment of the present invention is a rectangular prism, comprising: a fingerprint contacting surface 21 to be touched by a fingerprint 15 of a person; a totally reflecting surface 22 facing the fingerprint contacting surface 21 with an angle θ for totally and inwardly reflecting the light scattered from the fingerprint in contact with the fingerprint contacting surface 21; a primarily projecting/re-incident surface 23 linking the fingerprint contacting surface 21 with an angle φ to the totally reflecting surface 22 for primarily projecting the light totally reflected from the totally reflecting surface 22 so as to be re-incident from outside; and an ultimately projecting surface 24 facing the primarily projecting/re-incident surface 23 for ultimately projecting the light re-incident to the primarily projecting/re-incident surface 23 toward outside. The light projected from the ultimately projecting surface 24 is focused on an image sensor (not shown in the drawing) by the condensing lens 30 so as to be acquired as an image.

Meanwhile, a reflecting mirror 25 is installed outside adjacent to the primarily projecting/re-incident surface 23 at an angle δ. The reflecting mirror 25 reflects the light projected from the primarily projecting/re-incident surface 23 so as to be re-incident to the prism 20 through the primarily projecting/re-incident surface 23.

As shown in FIG. 2, the light source 40 irradiates light, which passes through the totally reflecting surface 22 of the prism and reaches a fingerprint 15 in contact with the fingerprint contacting surface. A detailed description of the operation of the light source 40 will be omitted here because it is the same as the conventional optical fingerprint acquisition apparatus.

Referring to FIG. 2, the light scattered from the fingerprint 15 is first totally and inwardly reflected from the totally reflecting surface 22. As shown in FIG. 2, the totally reflecting surface 22 is not parallel with the fingerprint contacting surface 21 but is oblique to have an angle θ therewith. Therefore, the light hit the totally reflecting surface 22 is totally reflected and orients the primarily projecting/re-incident surface 23.

The light totally reflected toward the primarily projecting/re-incident surface 23 penetrates the primarily projecting/re-incident surface 23, and is projected outside the prism 20. The projected light is reflected from the reflecting mirror 25 installed oblique with respect to the primarily projecting/re-incident surface 23, and re-incident thereto. Here, the reflecting mirror 25 is installed with an angle δ so that the light can orient the central portion of the ultimately projecting surface 24. The light reflected from the reflecting mirror 25 and re-incident to the prism 20 is projected outside the ultimately projecting surface 24, and incident to an image sensor (not shown in the drawing) through the condensing lens 30.

As described above, the optical paths of the light scattered from each position "a," "b," "c" of the fingerprint 15 and condensed onto the condensing lens are almost the same. Comparing the position "a" with the position "c," the optical path of the light scattered from the position "c" is longer than that of the light scattered from the position "a" until the light is totally reflected inside of the prism 20. However, the optical path of the light scattered from the position "a" is longer than that of the light scattered from the position "c" after the light is totally reflected from the totally reflecting surface 22. Accordingly, all the optical paths have almost the same lengths from any position of the fingerprint 15, and distortion of the fingerprint image can be reduced as a consequence.

Therefore, according to the present invention, it is critical how to determine the angle θ with the totally reflecting surface 22 as well as the angle δ with the reflecting mirror 25. The angle θ must be defined so as to totally reflect the light scattered from any position of an effective fingerprint contacting area E of the fingerprint contacting surface 21 toward the primarily projecting/re-incident surface 23, while the angle δ must be defined so as to reflect the light primarily projected from the primarily projecting/re-incident surface 23 toward the central portion of the ultimately projecting surface 24.

It is also preferable to consider the angle φ between the primarily projecting/re-incident surface 23 and the fingerprint contacting surface 21. The light passing between inside and outside of the prism 20 through the primarily projecting/re-incident surface 23 is refracted due to the refractive index of different media. Thus, it is preferable to determine the angle φ by considering the variation of the optical path of the light projected outside the prism 20 through the primarily projecting/re-incident surface 23, reflected from the reflecting mirror 25, and re-incident to the prism 20 through the primarily projecting/re-incident surface 23. Also, it is possible to fill in the space between the primarily projecting/re-incident surface 23 and the reflecting mirror 25 with a light transmissible material, although FIG. 2 does not show any material filled therebetween.

Meanwhile, the following relation is established among each surface of the prism 20 in FIG. 2.

(Length of the Ultimately Projecting Surface 24)<(Length of the Primarily Projecting/Re-Incident Surface 23)<(Length of the Fingerprint Contacting Surface 21)<(Length of the Totally Reflecting Surface 22)

The above relation is a natural consequence of forming the totally reflecting surface 22 to have an angle θ with the fingerprint contacting surface 21. This relation expresses a shape of the prism according to the present invention.

The optical fingerprint acquisition apparatus according to the present invention has advantages effects of increasing productivity, reducing the manufacturing cost and frequency of mis-operation by reducing distortion of a fingerprint image and minimizing the optical system without relying on a separate lens or a prism for image correction.

While the invention has been shown and described with reference to a certain preferred embodiment thereof, it will be understood by those skilled in the art that various changes in form and details may be made therein without departing from the spirit and scope of the invention as defined by the appended claims.

What is claimed is:

1. An optical fingerprint acquisition apparatus for acquiring a fingerprint image by light scattered from a fingerprint, the apparatus comprising:

a prism including a fingerprint contacting surface to be touched by a fingerprint of a person, a totally reflecting surface facing the fingerprint contacting surface with an angle $\theta$ for totally and inwardly reflecting the light scattered from the fingerprint in contact with the fingerprint contacting surface, a primarily projecting/re-incident surface linking the fingerprint contacting surface with an angle $\phi$ to the totally reflecting surface for primarily projecting the light totally reflected from the totally reflecting surface so as to be re-incident from outside the prism, and an ultimately projecting surface facing the primarily projecting/re-incident surface for ultimately projecting the light re-incident to the primarily projecting/re-incident surface toward the outside of the prism; and a reflecting mirror installed outside the prism, adjacent to the primarily projecting/re-incident surface of the prism and an angle $\delta$ thereto, the reflecting mirror for reflecting the light projected from the primarily projecting/re-incident surface so as to be re-incident to the prism through the primarily projecting/re-incident surface.

2. The optical fingerprint acquisition apparatus of claim 1, wherein the following relation is established among each surface of the prism:

(Length of the Ultimately Projecting Surface)<(Length of the Primarily Projecting/Re-Incident Surface)<(Length of the Fingerprint Contacting Surface)<(Length of the Totally Reflecting Surface).

3. The optical fingerprint acquisition apparatus of claim 2, wherein an angle $\theta$ between the fingerprint contacting surface and the totally reflecting surface is defined so as to totally reflect the light scattered at a predetermined angle from an effective fingerprint contacting area of the fingerprint contacting surface toward the primarily projecting/re-incident surface, the angle $\delta$ is defined so as to reflect all of the light primarily projected from the primarily projecting/re-incident surface toward a central portion of the ultimately projecting surface, and the angle $\phi$ is defined so as to refract all the light primarily projected from the primarily projecting/re-incident surface and reflecting from the reflecting mirror toward the central portion of the ultimately projecting surface.

4. The optical fingerprint acquisition apparatus of claim 2, wherein a light transmissible material is filled in the space between the primarily projecting/re-incident surface of the prism and the reflecting mirror.

5. The optical fingerprint acquisition apparatus of claim 1 wherein an angle $\theta$ between the fingerprint contacting surface and the totally reflecting surface is defined so as to totally reflect the light scattered at a predetermined angle from an effective fingerprint contacting area of the fingerprint contacting surface toward the primarily projecting/re-incident surface;

the angle $\delta$ is defined so as to reflect all of the light primarily projected form the primarily projecting/re-incident surface toward a central portion of the ultimately projecting surface, and the angle $\phi$ is defined so as to refract all the light primarily projected from the primarily projecting/re-incident surface and reflected from the reflecting mirror toward the central portion of the ultimately projecting surface.

6. The optical fingerprint acquisition apparatus of claim 1, wherein a light transmissible material is filled in the space between the primarily projecting/re-incident surface of the prism and the reflecting mirror.

* * * * *